(12) United States Patent
Barrett et al.

(10) Patent No.: US 9,308,306 B2
(45) Date of Patent: Apr. 12, 2016

(54) SELF CALIBRATING BLOOD CHAMBER

(71) Applicant: Fresenius Medical Care Holdings, Inc., Waltham, MA (US)

(72) Inventors: Louis Lee Barrett, West Point, UT (US); Perry N. Law, Kaysville, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 126 days.

(21) Appl. No.: 14/188,193

(22) Filed: Feb. 24, 2014

(65) Prior Publication Data

US 2015/0238672 A1 Aug. 27, 2015

(51) Int. Cl.
| | |
|---|---|
| *A61M 1/14* | (2006.01) |
| *G01N 21/59* | (2006.01) |
| *G01N 33/72* | (2006.01) |
| *A61M 1/36* | (2006.01) |

(52) U.S. Cl.
CPC .................. *A61M 1/14* (2013.01); *A61M 1/367* (2013.01); *A61M 1/3609* (2014.02); *A61M 1/3621* (2013.01); *G01N 21/59* (2013.01); *G01N 33/721* (2013.01); *A61M 2202/0413* (2013.01); *A61M 2205/3306* (2013.01); *A61M 2205/702* (2013.01); *A61M 2230/205* (2013.01); *A61M 2230/207* (2013.01); *G01N 2201/062* (2013.01)

(58) Field of Classification Search
CPC ............... A61M 2205/3306; A61M 2230/005; A61M 2230/205; A61M 1/14; A61M 2205/3592; A61M 2005/6063; A61M 2005/3327; A61M 1/3679; G01N 21/59; G01N 2201/062; G01N 33/721; G01N 21/05; G01N 21/274

USPC ............... 356/40, 432, 436, 39, 440, 437, 73, 356/246, 72, 433, 435, 317, 442, 341, 632, 356/239.2, 356, 70, 28; 436/66, 164, 805; 422/82.05, 82.09, 82.08; 250/216, 372, 250/343, 373

See application file for complete search history.

(56) References Cited

U.S. PATENT DOCUMENTS

| | | | |
|---|---|---|---|
| 5,214,593 A | * | 5/1993 | Magnussen, Jr ..... G01N 21/274 356/436 |
| 5,351,686 A | | 10/1994 | Steuer et al. |
| 5,372,136 A | | 12/1994 | Steuer et al. |

(Continued)

FOREIGN PATENT DOCUMENTS

WO    WO 2010/053627 A1    5/2010

OTHER PUBLICATIONS https://en.wikipedia.org/wiki/Fresnel_equations.*

(Continued)

*Primary Examiner* — Mohamed K Amara
(74) *Attorney, Agent, or Firm* — Leydig, Voit & Mayer, Ltd.

(57) ABSTRACT

An optical blood monitoring system and corresponding method avoid the need to obtain a precise intensity value of the light impinging upon the measured blood layer during the analysis. The system is operated to determine at least two optical measurements through blood layers of different thickness but otherwise substantially identical systems. Due to the equivalence of the systems, the two measurements can be compared so that the bulk extinction coefficient of the blood can be calculated based only on the known blood layer thicknesses and the two measurements. Reliable measurements of various blood parameters can thereby be determined without certain calibration steps.

3 Claims, 6 Drawing Sheets

(56) References Cited

U.S. PATENT DOCUMENTS

| | | | | |
|---|---|---|---|---|
| 5,760,900 A * | 6/1998 | Ito | G01N 15/1434 | 250/461.2 |
| 5,784,507 A * | 7/1998 | Holm-Kennedy | G01J 3/0259 | 250/227.23 |
| 6,169,604 B1 * | 1/2001 | Cao | G01J 3/26 | 356/519 |
| 6,292,298 B1 * | 9/2001 | Glance | G02B 6/29358 | 359/583 |
| 6,573,505 B2 * | 6/2003 | Richman | G01J 1/02 | 250/332 |
| 6,662,031 B1 * | 12/2003 | Khalil | A61B 5/0059 | 600/310 |
| 8,213,015 B2 * | 7/2012 | Kraizcek | B81C 1/00071 | 356/246 |
| 8,570,521 B2 * | 10/2013 | Chumachenko | G01N 21/0303 | 356/440 |
| 2002/0176068 A1 | 11/2002 | Fodgaard | | |
| 2006/0039009 A1 * | 2/2006 | Kiesel | G01J 9/0246 | 356/519 |
| 2008/0079942 A1 * | 4/2008 | Buettner | G01N 21/0303 | 356/436 |
| 2008/0186494 A1 * | 8/2008 | Kiesel | G01N 21/0303 | 356/440 |
| 2008/0186500 A1 * | 8/2008 | Schmidt | G01N 21/39 | 356/450 |
| 2009/0220189 A1 * | 9/2009 | Kiesel | G01J 3/02 | 385/12 |
| 2012/0288924 A1 | 11/2012 | Peterson et al. | | |
| 2014/0275949 A1 * | 9/2014 | Takahashi | A61B 5/02438 | 600/407 |
| 2014/0354998 A1 * | 12/2014 | Bock | A61M 5/31525 | 356/445 |

OTHER PUBLICATIONS

International Search Report and Written Opinion for co-pending International Application No. PCT/US2015/16785, dated Jun. 29, 2015.

* cited by examiner

SELF CALIBRATING BLOOD CHAMBER

FIELD

The present invention relates to blood monitoring systems for hemodialysis patients, and in particular, to methods of measuring hematocrit and/or estimating hemoglobin levels using a self-calibrating blood chamber. The same approach can be applied to measurement of other parameters as well, such as oxygen saturation and/or other analyte levels in the blood.

BACKGROUND OF THE INVENTION

Patients with kidney failure or partial kidney failure typically undergo hemodialysis treatment in order to remove toxins and excess fluids from their blood. To do this, blood is taken from a patient through an intake needle (or catheter) which draws blood from a vessel such as an artery located in a specifically accepted access location (for example, an arm, thigh, subclavian, etc.). The needle (or catheter) is connected to extracorporeal tubing that is fed to a peristaltic pump and then to a dialyzer which cleans the blood and removes excess water. The cleaned blood is then usually returned to the patient through additional extracorporeal tubing and another needle (or catheter). (In some cases, the blood may be returned to the body through the same extracorporeal connections as the intake—a mode called "single needle dialysis"). Sometimes, a heparin drip is located in the hemodialysis loop to prevent the blood from coagulating. By way of background, as the drawn blood passes through the dialyzer, it travels in straw-like tubes within the dialyzer which serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration while leaving the red cells in the blood stream, which cannot pass through the straw-like tubes due to physical size.

For patients undergoing hemodialysis treatment, it is typical to monitor the patient's blood using a blood monitoring system during the treatment. For example, an optical blood monitoring system may be used that employs optical techniques to non-invasively measure, in real-time, the hematocrit level of blood flowing through the hemodialysis system. In such a system, a blood chamber may be attached in-line to the extracorporeal tubing—usually on the arterial side of the dialyzer. The blood chamber provides a viewing point for optical sensors during the hemodialysis procedure. Wavelengths of light are directed through the blood chamber and the patient's blood flowing there through, and one or more photo detectors can be used to detect the resulting intensity of each wavelength. From the detected light intensity, a hematocrit value can be calculated and a hemoglobin level can be estimated.

BRIEF SUMMARY OF THE INVENTION

The present invention is directed to the use of an optical blood monitor including an optical blood sensor assembly and blood chamber that are constructed in a manner that reduces the complexity of, or eliminates the need for, calibrating the blood monitor to account for variance in the light intensity passing through the blood from one monitor to the next. This is achieved by making two optical measurements through the blood, where all variables between the two measurements are substantially identical except the distance that the light travels through the blood. A ratio of the two measurements can then be used to determine the values needed to calculate certain blood parameters without requiring a precise value of the light intensity emitted through the blood. Accordingly, various calibration procedures that are ordinarily required become unnecessary.

BRIEF DESCRIPTION OF THE SEVERAL VIEWS OF THE DRAWING(S)

Exemplary embodiments of the present invention are described in more detail below with reference to the drawings, in which.

DETAILED DESCRIPTION OF THE INVENTION

Figure 1:
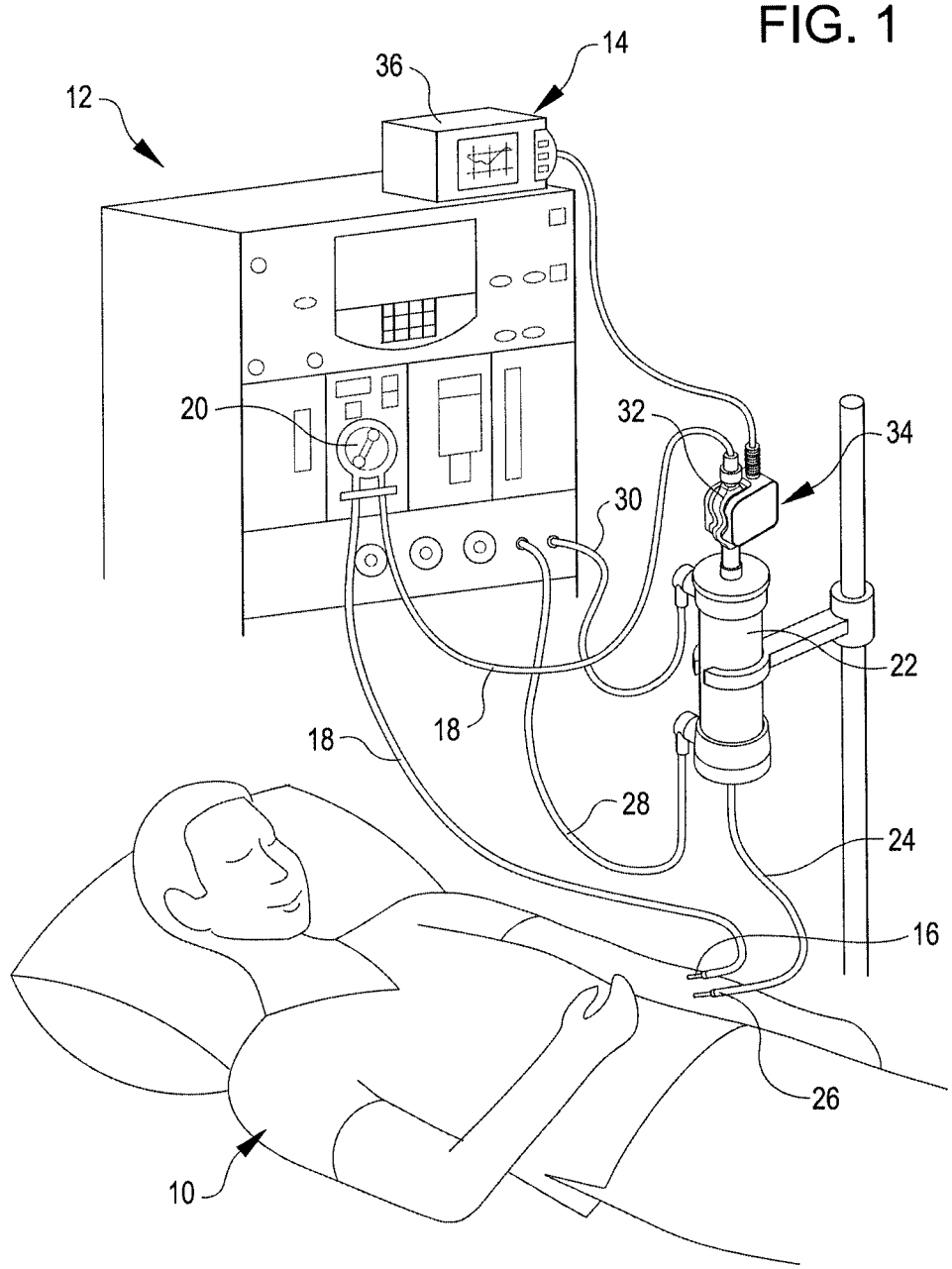
FIG. 1 shows a perspective view of a hemodialysis system that includes a blood monitor in accordance with an embodiment of the invention.

FIG. 1 illustrates a patient 10 undergoing hemodialysis treatment using a hemodialysis system 12, as well as a non-invasive, optical blood monitor 14. An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer through extracorporeal tubing 24 and return needle or catheter 26. Excess fluids and toxins are removed by clean dialysate liquid which is supplied to the dialyzer 22 via tube 28 and removed for disposal via tube 30. A typical hemodialysis treatment session takes about 3 to 5 hours in the United States.

The optical blood monitor 14 includes a blood chamber 32, an optical blood sensor assembly 34, and a controller 36. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light at substantially 810 nm, which is isobestic for red blood cell hemoglobin, substantially 1300 nm, which is isobestic for water, and at substantially 660 nm, which is sensitive to the oxygenation of hemoglobin. The blood chamber 32 includes lenses so that the sensor emitters and detectors can view the blood flowing through the blood chamber 32, and determine the patient's real-time hematocrit value and oxygen saturation value using ratiometric techniques generally known by those of ordinary skill in the art.

Figure 2:
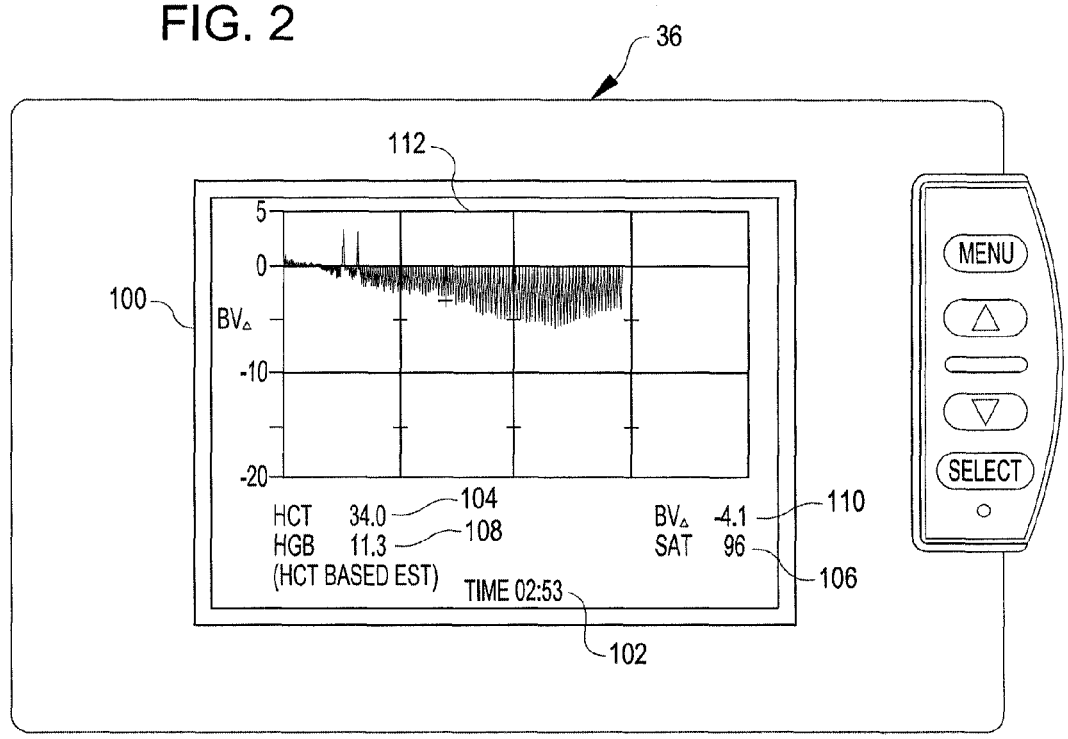
FIG. 2 shows a front view of a controller and display used with the blood monitor shown in FIG. 1.

FIG. 2 is a front view of a controller 36 for the optical blood monitor 14. The controller 36 includes a display 100 which provides real-time blood monitoring data for the patient undergoing hemodialysis. The display in FIG. 2 illustrates the amount of time 102 that the patient 10 has been monitored while undergoing hemodialysis for the current treatment session. The display 100 also illustrates real-time values for the optically monitored hematocrit (HCT) 104 and oxygen saturation (SAT) level 106, as well as calculated values for hemoglobin (HGB) 108 and change in blood volume (BVΔ) 110 during the treatment session. The graph 112 on the display 100 illustrates the change in the patient's blood volume over the course of the 2 hour and 53 minute treatment session. (Other variants of the graph 112 are possible such as showing a dual graph (upper and lower) with one displaying change in patient's blood volume and the other the patient's oxygen saturation.) These data are often displayed, as shown in FIG. 1, in a location that is located within the vicinity of the patient 10. These data can also be displayed at a central monitoring location via a wired or wireless system. Techniques that are used to obtain the values shown on display 100 are known to those of skill in the art. Certain aspects of these methods are particularly relevant to the methods and systems of the present invention and are described in further detail in the following.

LED emitters corresponding, for example, to the wavelengths described above, along with respective photodetectors for the optical blood monitor are positioned in place in the vicinity of the blood chamber. The wavelengths of light are directed through the blood chamber and the patient's blood flowing through the chamber so that the corresponding photodetector, typically the opposite side of the blood, can detect the resulting intensity of each wavelength. A ratiometric technique, substantially as disclosed in U.S. Pat. No. 5,372,136 entitled "System and Method for Non-Invasive Hematocrit Monitoring", which issued on Dec. 13, 1999 and is assigned to the assignee of the present application, uses this information to calculate the patient's hematocrit value in real-time. The hematocrit value, as is widely used in the art, is the percentage determined by dividing the volume of the red blood cells in a given whole blood sample by the overall volume of the blood sample.

In a clinical setting, the actual percentage change in blood volume occurring during hemodialysis can be determined, in real-time, from the change in the measured hematocrit. Thus, an optical blood monitor is able to non-invasively monitor not only the patient's hematocrit level but also the change in the patient's blood volume in real-time during a hemodialysis treatment session. The ability to monitor real-time change in blood volume helps facilitate safe, effective hemodialysis.

The mathematical ratiometric model for determining the hematocrit (HCT) value can be represented by the following equation:

$$HCT = f\left[\frac{\ln\left(\frac{i_{\lambda 2}}{I_{0-\lambda 2}}\right)}{\ln\left(\frac{i_{\lambda 1}}{I_{0-\lambda 1}}\right)}\right] \quad (1)$$

where $i_{\lambda 2}$ is the infrared light intensity detected by the photodetector at about 810 nm, is the infrared intensity detected at 1300 nm and $I_{0-\lambda 2}$ and $I_{0-\lambda 1}$ are constants representing the infrared light intensity incident on the blood accounting for losses through the blood chamber. The function f[ ] is a mathematical function which has been determined based on experimental data to yield the hematocrit value. Preferably, the function f[ ] in the above Equation (1) is a relatively simply polynomial, e.g. a second order polynomial. The above Equation (1) holds true only if the distance traveled by the infrared light radiation from the LED emitters to the photodetectors at both wavelengths are constant distances and preferably the same distance.

The preferred wavelengths to measure oxygen saturation level are about 660 nm and about 810 nm. The mathematical ratiometric model for determining oxygen saturation level (SAT) can be represented by the following equation:

$$SAT = g\left[\frac{\ln\left(\frac{i_{\lambda 3}}{I_{0-\lambda 3}}\right)}{\ln\left(\frac{i_{\lambda 1}}{I_{0-\lambda 1}}\right)}\right] \quad (2)$$

where $i_{\lambda 3}$ is the light intensity of the photodetector at 660 nm, $i_{\lambda 1}$ is the detected intensity at 810 nm and $I_{0-\lambda 3}$ and $I_{0-\lambda 1}$ are constants representing the intensity incident on the blood accounting for losses through the blood chamber. The function g[ ] is a mathematical function determined based on experimental data to yield the oxygen saturation level, again preferably a second order polynomial. Also, like Equation (1) for the hematocrit calculation, Equation (2) for the oxygen saturation level calculation holds true only if the distance traveled by the visible and infrared light from the respective LED emitter to the respective photodetector at both the 660 nm and 810 nm wavelengths are constant distances and preferably the same distance.

The above ratiometric models use constants to account for loss through the blood chamber to determine the light incident on the blood. The more general evaluation of light through the blood, or any other component of the optical system, is based on Beers Law, which is demonstrated by FIG. 3 and is set forth as follows with specific regard to a blood layer:

$$i = I_o e^{-\alpha d} \quad (3)$$

where:
i=the intensity of the received signal of the light after passing through the blood,
$I_o$=the impressed amplitude of the light wave as it enters the blood,
α=the bulk extinction term including the extinction coefficient of the blood and the concentration of the blood in the volume under test, and
d=the distance the light travels through the blood layer being tested.

Figure 3:
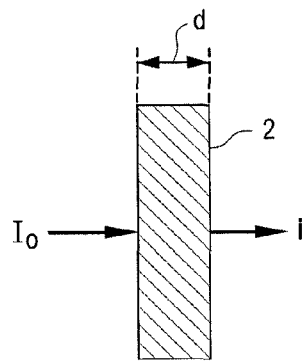
FIG. 3 shows the geometry corresponding to calculations used in optical blood monitoring.
Figure 4:
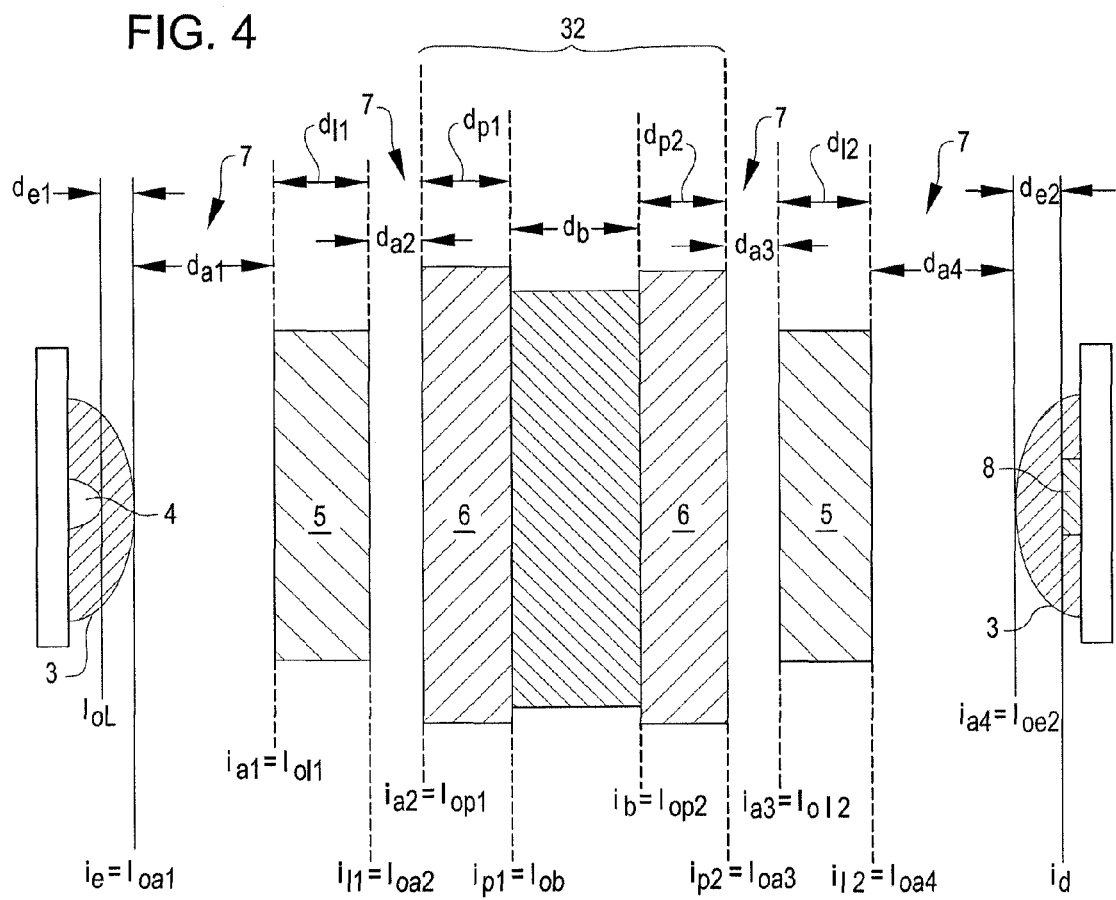
FIG. 4 shows the effect of the structure surrounding the blood on the calculations used in optical blood monitoring.

As illustrated in FIG. 3, the light enters the volume of blood that is being examined from one side with an intensity of $I_o$, passes through the blood 2 after travelling a distance d, and emerges from the volume of blood 2 with an intensity, i. In the idealized model shown in FIG. 3, the bulk extinction term α can be easily determined, from which hematocrit and oxygen saturation values can be determined by methods known to those of skill in the art. However, as illustrated by FIG. 4, obtaining the amplitude of the light that enters the volume of blood within the blood monitoring chamber is not trivial. Each of the elements in the optical path between the light emission element 4 and the light sensor 8 must be accounted for in the analysis. In the example illustrated in FIG. 4, these elements include a layer of epoxy 3 disposed over each of the light emission element 4 and the light sensor 8, a lens 5 disposed on each side of the blood chamber 32, each of the blood chamber walls 6, and air gaps 7 on either side of each lens. Thus, the evaluation of the complete optical path includes the application of Beers Law for each of these ten components as well as the blood itself.

The foregoing eleven different applications of Beers Law can be combined due to the evident relationship of the received and emitted light at each boundary. Specifically, because the light being emitted from one layer is the same as the light being received at the subsequent layer, these terms are equal and thus, can be substituted for one another. An example of the combining of the application of Beers Law for two layers is illustrated by equations (4) through (6). Equation (4) is a representation of Beers Law for the intensity of the light $i_{a1}$ being emitted from the first air gap 7 shown in FIG. 4. As shown in equation (4), the light emitted from the first air gap $i_{a1}$ is a function according to Beers Law of the light received at the air gap $I_{oa1}$.

$$i_{a1} = I_{oa1} e^{-\alpha_a d_{a1}} \quad (4)$$

where:
$i_{a1}$=the intensity of the light after passing through the first air gap,
$I_{oa1}$=the impressed amplitude of the light wave as it enters the first air gap,
$\alpha_a$=the bulk extinction term for the first air gap, and
$d_{a1}$=the distance the light travels through the first air gap.

Further, as shown in FIG. 4, and stated previously, the light being received at the air gap $I_{oa1}$ is the same as the light being emitted from the epoxy $i_e$, which can be expressed as a function of the light emitted from the light source $I_{oL}$, as shown in equation (5).

$$I_{oa1} = i_e = I_{oL} e^{-\alpha_e d_{e1}} \quad (5)$$

where:
$i_e$=the intensity of the light after passing through the first epoxy layer,
$I_{oL}$=the impressed amplitude of the light wave as it enters the first epoxy layer,
$\alpha_e$=the bulk extinction term for the first epoxy layer, and
$d_e$=the distance the light travels through the first epoxy layer.

Accordingly, by substituting the function from equation (5) into the unknown value for $I_{oa1}$ in equation (4), the intensity of the light being emitted from the first air gap $i_{a1}$ can be expressed as a compound form of Beers Law, yielding equation (6), where the intensity of the light after the first air gap is expressed as a function of the light from the light source $I_{oL}$ and the constants related to the epoxy layer and air gap, as follows:

$$i_{a1} = (I_{oL} e^{-\alpha_e d_{e1}}) e^{-\alpha_a d_{a1}} \quad (6)$$

The foregoing substitution can be applied for all eleven components in the optical path to arrive at a single equation for the intensity of the light received at the detector $i_d$ based on the emitted light from the light element $I_{oL}$. This single equation (7) is shown below, where each of the ten optical components has been represented with a numerical reference except for the blood layer component ($e^{-\alpha_b d_b}$), as follows:

$$i_d = I_{oL}[e^{-\alpha_1 d_1} e^{-\alpha_2 d_2} e^{-\alpha_3 d_3} e^{-\alpha_4 d_4} e^{-\alpha_5 d_5} (e^{-\alpha_b d_b})$$
$$e^{-\alpha_6 d_6} e^{-\alpha_7 d_7} e^{-\alpha_8 d_8} e^{-\alpha_9 d_9} e^{-\alpha_{10} d_{10}}] \quad (7)$$

The static components of the optical path are substantially invariable with respect to time, and thus their contributions can be considered constant. As such, equation (7) can be rewritten with all of the components of the epoxy layers, air gaps, lenses and chamber walls being represented by a single constant value A, as shown in equation (8).

$$i_d = I_{oL} A e^{-\alpha_b d_b} \quad (8)$$

Figure 9:
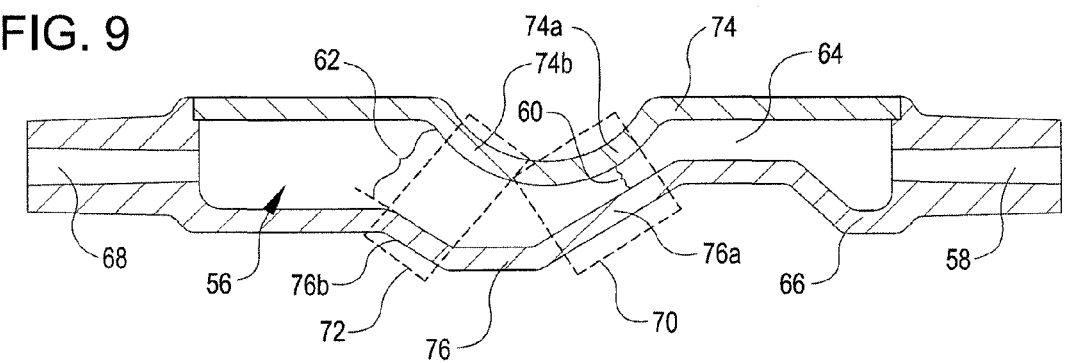
FIG. 9 shows a cross sectional view of the blood chamber of FIG. 8.

Moreover, since the intensity of the light emitted by the light emission element is consistent from one reading to the next, the constant A can be combined with the emitted light intensity $I_{oL}$ into a modified light intensity $I_{oT}$ as shown in FIG. 9).

$$i_d = I_{oT} e^{-\alpha_b d_b} \quad (9)$$

Thus, as illustrated by equation (9) the intensity of the received signal at the light sensor varies based solely on the bulk extinction coefficient for the blood $\alpha_b$ for a given thickness of the measured blood and can be calculated so long as $I_{oT}$ is known.

However, calculating $I_{oT}$ is not trivial, as it is based on the bulk extinction coefficient of each of the optical components disposed in the optical path from the light emission element 4 to the light detector 8. In view of the large number of components disposed between the emission element 4 and light detector 8, small variances in each these components, based merely on manufacturing tolerances, cause uncertainty in the value of $L_T$ from one blood monitor to the next. To address these variances, blood monitors are typically calibrated and then validated in a laboratory using actual human blood from a blood bank to determine the appropriate constants for use with each particular blood monitor. This process is long, laborious and expensive, and attaining blood can be difficult.

The present invention is directed to an optical blood monitoring system and corresponding method that avoid the need to obtain a precise intensity value of the light impinging upon the blood layer. This is achieved by taking at least two optical measurements through blood layers of different thickness but using the same light source for each measurement. Due to the difference in thickness, each of the measurements can be represented by a different equation, where the terms for the blood layer thickness and the received signal differ. However, the terms for both the intensity of the light impinging upon the blood layer and the bulk extinction coefficient of all the optical elements in the system, aside from the blood, are the same in both models. For this reason, the two equations can be combined and the redundant terms can be removed in order to solve for the bulk extinction coefficient of the blood based only on the known blood layer thicknesses and the corresponding two measurements.

In an embodiment, the present invention provides a blood monitor with a light emission element that projects light along two identical optical paths but through blood layers of different thickness. Each path is directed to a respective light sensor that measures the intensity of the light that has passes through the respective blood layer thickness. Preferably, the positions of the two optical paths are situated such that the intensity of the impressed light from the light emission element is the same along both paths. Consequently, so long as the other components in the blood monitor optical paths are constructed substantially identically, the intensity of the light being directed into the blood layer along each path will be substantially identical. The components for receiving light intensity are equal in sensitivity and are integrated into equal optical paths for measurement of the light after blood penetration for each of the two path measurements. This equivalence allows the components representing the received light intensity to be removed from a mathematical model that is representative of a combination of the two measurements, as explained in detail below.

As already described, light passing through a layer of blood of thickness d can be represented by equation (9). Thus, two optical paths, passing through blood layers of thickness $d_{b1}$ and $d_{b2}$ can be represented by equations (9a) and (9b), where the measured signals will differ due to the difference in only the blood layer thickness.

$$i^{d1}=I_{oT}e^{-\alpha bdb1} \qquad (9a)$$

$$i_{d2}=I_{oT}e^{-\alpha bdb2} \qquad (9b)$$

Dividing (9a) from (9b) allows the equations to be combined, so that the light impingement term $L_{oT}$ is included in both the numerator and denominator and can therefore be removed, as shown in equation (10)

$$\frac{i_{d1}}{i_{d2}} = \frac{I_{oT}e^{-\alpha_b d_{b1}}}{I_{oT}e^{-\alpha_b d_{b2}}} = e^{-\alpha_b d_{b1}+\alpha_b d_{b2}} = e^{\alpha_b(d_{b2}-d_{b1})} \qquad (10)$$

Taking the natural log of equation (10) allows the bulk extinction coefficient of the blood $\alpha_b$ to be isolated and determined based only on the measured signals and respective blood thicknesses without requiring a value for the light impingement term, as shown in equation (11).

$$\alpha_b = \frac{\ln\left(\frac{i_{d1}}{i_{d2}}\right)}{(d_{b2}-d_{b1})} \qquad (11)$$

Based on equation (11) it can be seen that the difference in thickness between the two measured blood layers is an important value for determining the bulk extinction coefficient of the blood. Accordingly, it is preferable to make the difference in thickness substantial. In preferred embodiments, the thickness of the second blood layer is at least twice the thickness of the first blood layer. However, the mathematical evaluation of the detected light signal is very sensitive to the thickness of the blood layer, and thus, the difference in thickness $(d_{b2}-d_{b1})$ must be considered carefully. When the difference in thickness of the blood layer is very small, the influence of manufacturing tolerances can be dramatic, as very slight variances in manufacturing of the chamber thickness can result in significant variance in the measured values. On the other hand, as the difference in thickness of the blood layers increases, the strength of the signal of detected light diminishes exponentially in the channel with the widest gap thereby limiting the blood range over which measurements are possible due to the required dynamic range of the receiver system. Accordingly, large thicknesses in the blood chamber can also result in unreliable data due to limits in measuring small signals. Thus, while it is beneficial for the thickness of the first and second blood layers to be significantly different, each layer must fall within a relatively narrow range of operable dimensions that are needed to collect accurate data.

In order to take advantage of the above relationship of the two measurements, all of the terms from equation (7), except the term corresponding to the blood $e^{\alpha a_b d_b}$ and the measured light signal $i_d$, must be substantially identical for each of the two optical paths. Thus, the intensity of the light being emitted along each optical path and the thickness and bulk extinction coefficient of all of the optical components (except the blood) between the light source and the light sensor should be substantially identical for both optical paths.

Figure 5:
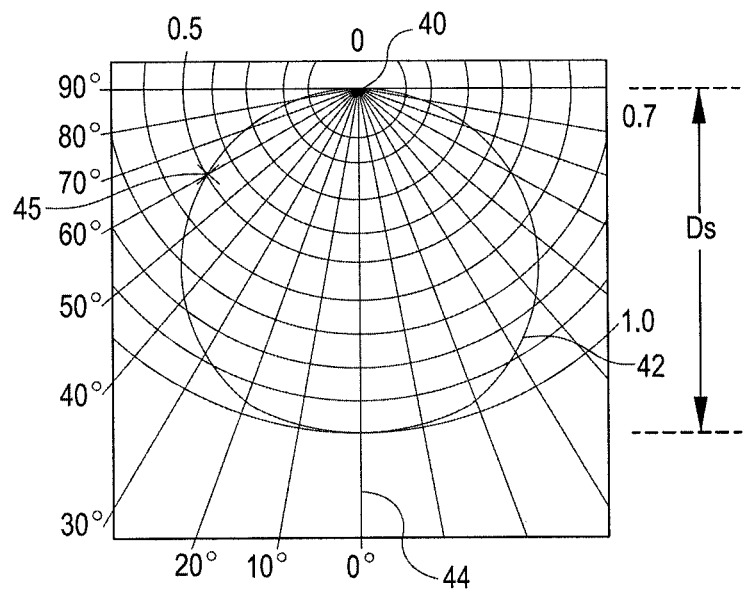
FIG. 5 shows a sample radiation pattern from a light source.

The light intensity along each of the two optical paths can be made equal by using a single light source with a known light pattern for both of the paths. As illustrated in FIG. 5, the intensity of light being emitted from a typical light source, such as the shown light emitting diode and lens, is strongest along a central axis extending from the light source. At angles that diverge from this axis, the intensity of the light decays. In FIG. 5, the solid line 42 is representative of the polar intensity of the light being emitted from light source 40 referenced in angle to the center of the source. At an arbitrary distance from the source (Ds), the maximum intensity along the central axis is normalized to a value of 1.0. As can be seen in the figure, the illumination along the central axis 44 is strongest and the designated intensity by the normalized arc 42 at this location is 1.0. In contrast, the light provided at the distance Ds from the source and at an angle of 60° from the central illumination axis 44, corresponding to point 45 on the normalized light intensity diagram, is half the maximum intensity and corresponds to an intensity of 0.5.

An important aspect illustrated by FIG. 5 is the symmetry of the decay in light intensity on either side of the illumination axis at a fixed distance Ds. Embodiments of the present invention utilize this equivalence to provide identical light intensity along both of the optical paths being used in this optical system. Specifically, a single light source can be used to provide illumination along each of two optical paths that are oriented at the same angle from the illumination axis and the same distance from the illumination source. Based on the light radiation pattern shown in FIG. 5, the use of such symmetrical optical paths provides light intensities that are reliably identical in intensity. This method is considerably more reliable than using two different light sources that are merely rated at the same light intensity, and it further eliminates the need to calibrate the system to account for any differences in intensity that are practically inevitable if using separate light sources. Further, use of a single light source removes any issues with spectral difference that could arise when separate sources are used.

To make the bulk extinction coefficients identical for all of the optical components along both optical paths, the optical blood monitor is designed to utilize a single blood chamber with areas that accommodate blood layers of different thickness and receive light along the two separate optical paths. Aside from the differences in the two blood layer sections, the components of the blood chamber are made substantially identical, to ensure identical bulk extinction coefficients of the static optical components within both paths.

Figure 6:
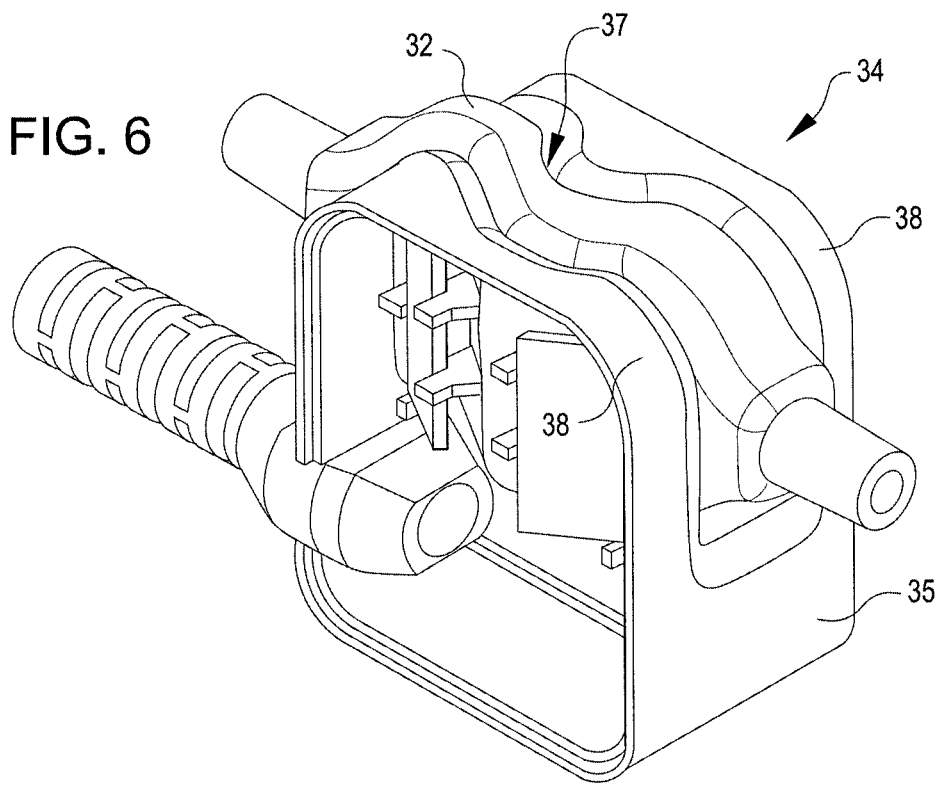
FIG. 6 shows a perspective view of an optical blood monitor sensor in accordance with an embodiment of the invention.
Figure 7:
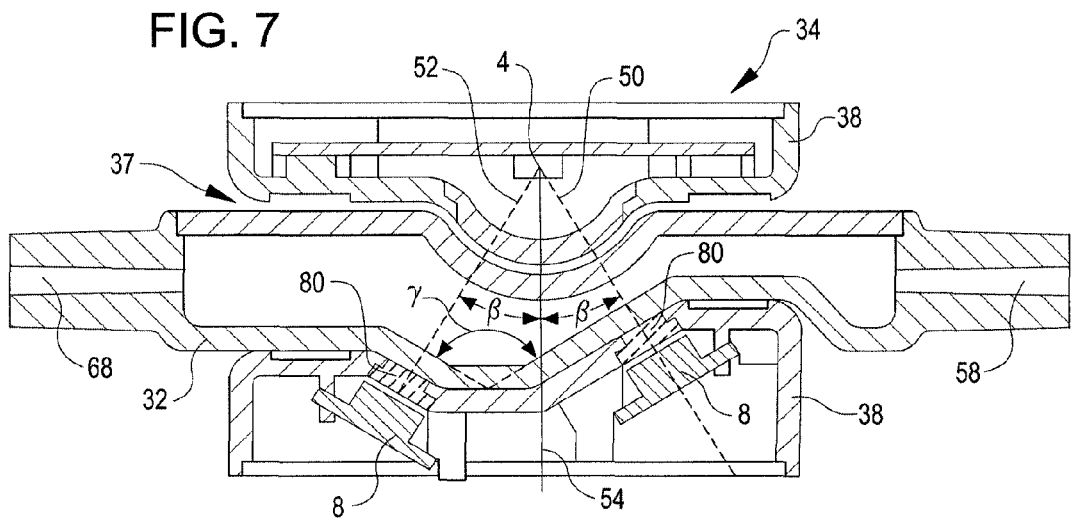
FIG. 7 shows a cross sectional view of the optical blood monitor sensor of FIG. 6.

FIGS. 6 and 7 illustrate an optical blood monitor 14 in accordance with an embodiment of the present invention. The blood monitor 14 includes an optical blood sensor 34 and a blood chamber 32. The optical sensor assembly 34 includes at least one light emission element 4 that provides light along two separate paths through the blood chamber 32. In a typical embodiment, the optical blood sensor assembly 34 may in fact include multiple different light elements disposed at the same cross section of the blood chamber with respect to the blood flow. The different light emission elements could thereby be configured to emit different wavelengths of light, which is advantageous for collecting optical blood data. An important aspect of the present embodiment, however, is that the respective wavelength light emission elements, emit light along two different optical paths for making measurements of the blood.

The assembly 34 shown in FIGS. 6 and 7 includes a housing 35 configured as a clamp or frame that receives the blood chamber 32 in a cavity 37 disposed between two jaws 38. The jaws 38 can be biased toward one another to secure the blood chamber 32 in place, or can be configured in any way in order to fit securely around the chamber 32.

When the blood chamber 32 is disposed in the assembly 34, the light emission element 4 is configured to emit light through the blood chamber 32 along first and second optical paths 50, 52 that are disposed at an angle with respect to one another. The description of two elements or components as being disposed "at an angle" to one another, as used herein, identifies the components as being neither aligned nor parallel. Thus, the phrase "at an angle" precludes angles of 0 degrees or 180 degrees. Instead, as used herein, two components are disposed "at an angle" to one another if the components are angled at between 3 degrees and 177 degrees with respect to one another. Preferably, the particular geometric relationship of the first and second optical paths is established to provide light along these paths at substantially identical intensities. To achieve this similarity of light intensity, the two optical paths may be symmetrically disposed on either side of an axis 54 of the light emission element 4 at substantially identical angles β from the axis 54, as implied by the light intensity plot show in FIG. 5. Each of the optical paths 50, 52 is directed to a respective light sensor 8 disposed on the assembly housing 35. In the illustrated embodiment, the light emission element 4 is disposed on a first jaw 38 of the housing 35 and the sensors 8 are disposed on the other jaw 38 of the assembly housing opposite the cavity 37 containing the blood chamber 32.

Figure 8:
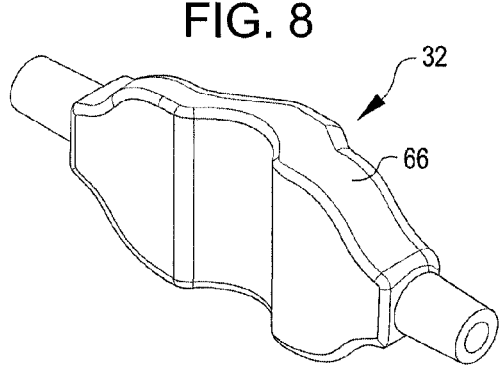
FIG. 8 shows a perspective view of a blood chamber in accordance with an embodiment of the invention.

During operation, the blood chamber 32 is disposed within the cavity 37 of the optical blood sensor assembly 34 and receives a flow of blood which is analyzed using the light emission element 4 and sensors 8. The blood chamber 32 is shown in FIGS. 8 and 9 and includes an internal volume 56 that is filled with blood through an inlet 58 and is drained through an outlet 68. The internal volume 56 is specifically designed to provide first and second blood layers 60, 62 of different thickness within the respective optical paths 50, 52 of the light being emitted by element 4 and received by sensors 8. The blood layers 60, 62 are formed by the geometry of the internal volume 64 of the blood chamber, which is determined by the shape of the body 66 of the blood chamber 32. Specifically, the blood chamber 32 includes first and second sections 70, 72 that provide the respective blood layers 60, 62 within the internal volume 56.

Preferably, the body 66 of the blood chamber 32 includes two opposing walls 74, 76 that substantially define the shape of the internal volume 56 and the orientation and thickness of the respective first and second sections 70, 72. Each of the walls 74, 76 is oriented within the optical blood sensor assembly 32 to correspond to one of the assembly's jaws 38. Thus, the first wall 74 is disposed on the side of the assembly 32 that incorporates the light emission element 4 and the second wall 76 is disposed on the side of the assembly 32 that houses the sensors 8. Moreover, the walls 74, 76 respectively provide the boundaries on the light inlet side and light outlet side of the blood chamber sections 70, 72. Specifically, the first wall 74, disposed on the light inlet side of the chamber near the light emitting element, includes a first region 74a that forms part of the first section 70 of the chamber and a second region 74b that forms part of the second section 72 of the blood chamber. Likewise, the second wall 76 has a first region 76a that defines part of the first section 70 and a second region 76b that defines part of the second section 72 of the blood chamber.

Advantageously, the two walls 74, 76 can be constructed as a continuous piece so that the composition and thickness of each wall can reliably be made the same in both respective first regions 74a, 76a and second regions 74b, 76b. Moreover, the respective first and second regions of each wall 74, 76 can be fashioned to intersect the respective first and second optical paths 50, 52 at the same angle as illustrated in FIG. 7. Preferably, both of the walls 74, 76 are shaped so that the optical paths intersect the respective regions of the walls orthogonally. The term "orthogonal" is used herein to mean intersecting at approximately a right angle, for example at an angle between 85° and 95°. Due to the identical intersection of the first optical path with each of the first regions, and the identical intersection of the second optical path with each of the second regions, the first region of each wall is disposed at the same angle γ with respect to the second region of that respective wall.

As a consequence of making each of the blood chamber walls 74, 76 as a single piece, so that the respective first and second regions have identical thickness and composition, and by orienting the respective regions at the same angle with respect to the optical paths, the body 66 of the blood chamber is formed to reliably have a substantially identical influence on the light in each optical path 50, 52. Thus, while the thickness of the blood layer is different for each section 70, 72 of the blood chamber, the optical impact of the regions of the blood chamber body that are disposed within the optical paths is substantially identical. Consequently, the bulk extinction coefficient of the blood chamber itself is the same for each optical path.

Preferably, the optical blood sensor assembly is also constructed to have a substantially identical influence on the light along each optical path 50, 52. This can be achieved by using the same principles as those applied to the blood chamber, for example by making the lens 80 as a single piece that intersects each of the optical paths at the same angle. Likewise, the optical sensors 8 are preferably positioned at the same distance from the second wall 76 of the blood chamber and are oriented at the same angle with respect to the respective optical path. Again, this similarity of the elements along each optical path allow the optical blood monitor to have the same influence on the light along each path, so that the corresponding terms can be removed from the analysis, as explained above.

Figure 10:
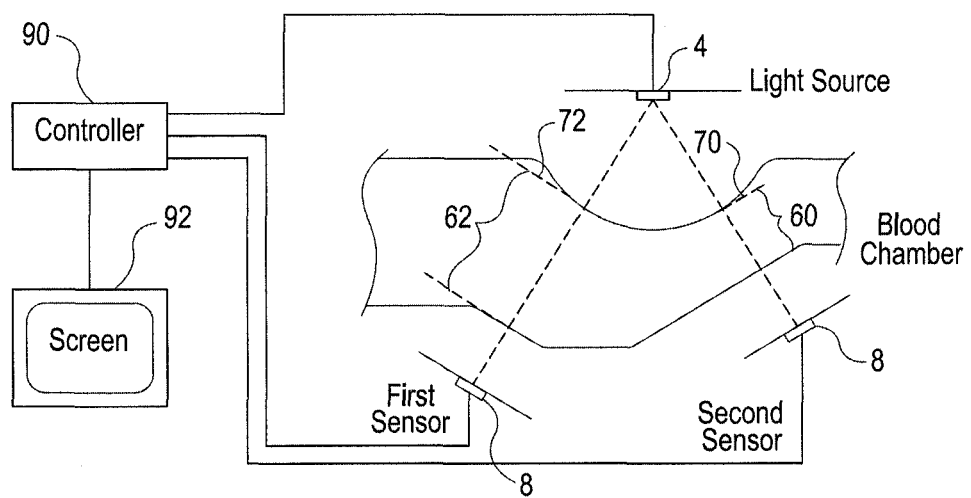
FIG. 10 shows a control system for operating a blood monitor in accordance with an embodiment of the present invention.

During operation, the optical blood monitor 14 is used to determine several blood parameters based on signals provided by the two light sensors 8. The blood being removed from the patient for hemodialysis treatment is diverted to the blood monitor 14 before being returned to the patient. Within the blood monitor 14, the blood is pumped through the internal volume 56 of the blood chamber 32 where the first and second blood layers are formed. At least one light emitting element 4 is operated by a controller 90, as shown in FIG. 10, to provide a light signal along two optical paths that respectively pass through each of the first and second blood layers 60, 62. The light projected along each optical path is subsequently received by respective light sensors 8 disposed in each path. Each of the light sensors produces a signal that is indicative of the influence of the blood within the respective layer on the intensity of the light. The signals are passed to the controller 90, which evaluates the signals to determine the bulk extinction coefficient of the blood $\alpha_b$ at each of the wavelengths, as explained in detail above. Based on the bulk extinction coefficient $\alpha_b$ ratios and the appropriate wavelengths, the controller 90 is able to determine various blood parameters, such as hematocrit, estimated hemoglobin, oxygen saturation and change in blood volume, which are then presented on a display 92.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims)

are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A blood chamber for use in a hemodialysis system operable to monitor at least one blood constituent, the blood chamber comprising a body defining an internal volume for receiving blood to be monitored by the hemodialysis system, the body including:

a first wall, disposed on a light inlet side of the body, configured to pass light from a light source into the internal volume;
a second wall, disposed on a light outlet side of the body, configured to pass the light from the light source out of the internal volume towards light sensors;
an inlet for supplying blood to the internal volume; and
an outlet for withdrawing blood from the internal volume;
wherein the blood chamber provides a first optical path extending through the body for the light from the light source, the first optical path orthogonally traversing a region of the first wall, passing through a section of the internal volume that has a first thickness extending from the first wall to the second wall, and orthogonally traversing a section of the second wall;
wherein the blood chamber further provides a second optical path extending through the body for the light from the light source, the second optical path orthogonally traversing another region of the first wall, passing through a section of the internal volume that has a second thickness extending from the first wall to the second wall, and orthogonally traversing another region of the second wall, wherein the second thickness is substantially greater than the first thickness and the first and second optical paths are disposed at an angle;
wherein the region of the first wall that is traversed by the first optical path is disposed at a non-zero angle $\gamma$ to the region of the first wall that is traversed by the second optical path, and wherein the region of the second wall that is traversed by the first optical path is disposed at the non-zero angle $\gamma$ to the region of the second wall that is traversed by the second optical path; and
wherein the first and second optical paths are disposed on either side of an axis through the light source and pass through the internal volume where blood flows through the blood chamber.

2. The blood chamber recited in claim 1, wherein the region of the first wall that is traversed by the first optical path has an equal thickness to the region of the first wall that is traversed by the second optical path.

3. The blood chamber recited in claim 1, wherein the region of the second wall that is traversed by the first optical path has an equal thickness to the region of the second wall that is traversed by the second optical path.

* * * * *